(12) United States Patent
Rossman et al.

(10) Patent No.: US 12,357,469 B2
(45) Date of Patent: Jul. 15, 2025

(54) SYSTEM AND METHOD OF TREATMENT OF BONE LESIONS

(71) Applicant: SpineSmith Partners, L.P., Austin, TX (US)

(72) Inventors: John B. Rossman, Austin, TX (US); Dru Dunworth, Austin, TX (US); Nathan Drawe, Boerne, TX (US)

(73) Assignee: SpineSmith Partners, L.P., Austin, TX (US)

( * ) Notice: Subject to any disclaimer, the term of this patent is extended or adjusted under 35 U.S.C. 154(b) by 1116 days.

(21) Appl. No.: 14/942,853

(22) Filed: Nov. 16, 2015

(65) Prior Publication Data

US 2016/0135819 A1    May 19, 2016

Related U.S. Application Data

(60) Provisional application No. 62/080,360, filed on Nov. 16, 2014.

(51) Int. Cl.
*A61F 2/46* (2006.01)
*A61B 17/16* (2006.01)
(Continued)

(52) U.S. Cl.
CPC ........ *A61F 2/4601* (2013.01); *A61B 17/1721* (2013.01); *A61B 17/1635* (2013.01);
(Continued)

(58) Field of Classification Search
CPC ........ A61F 2/4601; A61F 2/3859; A61F 2/28; A61F 2/30756; A61F 2002/2828;
(Continued)

(56) References Cited

U.S. PATENT DOCUMENTS

| 5,306,311 A * | 4/1994 | Stone | A61F 2/28 623/14.12 |
| 2002/0050045 A1* | 5/2002 | Chiodo | H01R 13/633 29/426.5 |

(Continued)

OTHER PUBLICATIONS

Hakimi M, Grassmann JP, Betsch M, Schneppendahl J, Gehrmann S, et al. (2014) The Composite of Bone Marrow Concentrate and PRP as an Alternative to Autologous Bone Grafting. PLOS One 9(6): e100143. https://doi.org/10.1371/journal.pone.0100143. (Year: 2014).*

(Continued)

*Primary Examiner* — Marcela I. Shirsat
(74) *Attorney, Agent, or Firm* — Winstead PC (57) ABSTRACT

The present disclosure describes a method and device for treatment of bone lesions. The device may include a combination of a drill device, a drill guide, a guide wire, and a syringe. The drill device includes a cannula through which a substance may be injected, an attachment head, and a drill bit. The attachment head may include a fitting for a powered or manual drill and a luer fitting for attaching a syringe or other device. The drill guide includes a cannula with an inner diameter sized to accommodate the cannula of the drill device. The method may include: placing a drill guide near a bone-lesion site, inserting a guide wire through the drill guide, inserting a drill device into the drill guide, removing the guide wire, drilling the bone, and injecting a cellular component and a retention medium into the bone near the lesion site.

12 Claims, 7 Drawing Sheets

(51) Int. Cl.
  *A61B 17/17* (2006.01)
  *A61B 17/56* (2006.01)
  *A61B 17/74* (2006.01)
  *A61B 17/88* (2006.01)
  *A61F 2/28* (2006.01)
  *A61F 2/30* (2006.01)
  *A61K 35/35* (2015.01)

(52) U.S. Cl.
  CPC ....... *A61B 17/1637* (2013.01); *A61B 17/1668* (2013.01); *A61B 17/1697* (2013.01); *A61B 17/1703* (2013.01); *A61B 17/1742* (2013.01); *A61B 2017/564* (2013.01); *A61B 17/742* (2013.01); *A61B 17/8805* (2013.01); *A61B 17/8833* (2013.01); *A61F 2002/2828* (2013.01); *A61F 2002/2832* (2013.01); *A61F 2002/30057* (2013.01); *A61F 2002/30766* (2013.01); *A61K 35/35* (2013.01)

(58) Field of Classification Search
  CPC .... A61F 2002/2832; A61F 2002/30766; A61F 2002/30059; A61F 2002/30057; A61F 2002/2825; A61B 17/1721; A61B 17/74; A61B 17/742; A61B 17/1668; A61B 17/56; A61B 17/1742; A61B 2017/564; A61B 17/8802; A61B 17/8805; A61B 17/8833; A61B 17/1635; A61B 17/1637; A61B 17/1697; A61B 17/1703; A61K 35/35
  USPC .......................................................... 606/80
  See application file for complete search history.

(56) References Cited

U.S. PATENT DOCUMENTS

| | | | | |
|---|---|---|---|---|
| 2004/0101960 A1* | 5/2004 | Schaefer | ................ | A61L 27/50 435/366 |
| 2005/0107800 A1* | 5/2005 | Frankel | .............. | A61B 17/1655 606/92 |
| 2007/0055276 A1* | 3/2007 | Edidin | ............... | A61B 17/8855 606/92 |
| 2008/0033572 A1* | 2/2008 | D'Antonio | ............. | A61K 35/32 623/23.51 |
| 2008/0269762 A1* | 10/2008 | Simon | .................... | A61B 17/56 606/99 |
| 2009/0036838 A1* | 2/2009 | Quelle | ................ | A61L 27/3839 604/207 |
| 2011/0125265 A1* | 5/2011 | Bagga | ................ | A61B 17/7098 623/16.11 |
| 2011/0218513 A1* | 9/2011 | Walker | ............... | A61B 17/8816 604/500 |
| 2013/0030547 A1* | 1/2013 | Burkinshaw | .............. | A61F 2/28 623/23.63 |
| 2013/0110115 A1* | 5/2013 | Lackman | ........... | A61B 17/8805 606/94 |
| 2014/0219982 A1* | 8/2014 | Matsubara | ............. | A61K 38/54 424/94.2 |
| 2015/0044272 A1* | 2/2015 | Kushnir | .................. | A61L 15/44 424/529 |
| 2015/0065947 A1* | 3/2015 | Wallace | ................. | A61K 35/44 604/22 |
| 2015/0297316 A1* | 10/2015 | Grinstaff | ................ | A61B 10/04 600/431 |

OTHER PUBLICATIONS

Kalka et al (Kalka C, Masuda H, Takahashi T et al (2000) Tranplatnation of ex vivo endothelial progenitor cells for therapeutic neovascularization. Proceedings of the National Academy of Sciences Mar. 2000, 97 (7) 3422-3427. https://www.pnas.org/content/97/7/3422.full; last accessed on Aug. 26, 2020. (Year: 2000).*

K. Cheng, T. Kuo, K. Kuo, C. Hsiao "Human adipose-derived stem cells: Isolation, characterization and current application in regeneration medicine" Genomic Medicine, Biomarkers, and Health Sciences, 3 (2) (2011), pp. 53-62. https://doi.org/10.1016/j.gmbhs.2011.08.003; last accessed on Nov. 3, 2020 (Year: 2011).*

Shah, F.S., Wu, X., Dietrich, M., Rood, J., Gimble, J.M., 2013. A non-enzymatic method for isolating human adipose tissue-derived stromal stem cells. Cytotherapy 15, 979-985. https://doi.org/10.1016/j.jcyt.2013.04.001. Las accessed Dec. 17, 2020 (Year: 2013).*

* cited by examiner

SYSTEM AND METHOD OF TREATMENT OF BONE LESIONS

CROSS-REFERENCES TO RELATED APPLICATIONS

This application claims the benefit under 35 U.S.C. § 119(e) of U.S. Provisional Patent Application No. 62/080,360, filed Nov. 16, 2014, which is incorporated herein by reference in its entirety as if fully set forth herein.

TECHNICAL FIELD OF THE INVENTION

The present disclosure relates generally to the field of medicine. More particularly, it concerns treatment of joint pain through treatment bone lesions.

BACKGROUND OF THE INVENTION

Joint pain and inflammation is a common malady amongst patients across the world. In the past, treatment has focused on attempting to repair cartilage within the joint. Damaged cartilage and discs have been treated by such methods as debridement, fusion, or arthroscopic surgery. Although these methods have been shown in some patients to provide temporary pain relief, they fail to treat the potential underlying cause of the pain. This invention is a method for treating joint pain and inflammation by treating adjacent subchondral bone marrow lesions via a method that promotes cell retention which retains cells at the site of pathology.

Bone lesions are comprised of several types, including bone marrow lesions (BMLs), edema, bone bruises, osteonecrosis, etc. These pathologies are localized to specific areas of trabecular bone that frequently become necrotic or damaged due to excessive mechanical trauma, although the pathology of such lesions is not well established. They are often defined in different manners in different locations of the body. For example in the hip or shoulder the lesions are often identified as Avascular Necrosis (AVN). While not well defied, causes of AVN include damage by physical trauma, degradation by natural causes or chemically-induced degradation (e.g., cortico-steroid use, chemotherapy, or radiation). Bone marrow lesions can lead to arthritis of the joint and/or collapse of the bone, each of which can result in significant joint pain. The proposed invention provides a method of treatment of the bone lesions and unique tools to perform the associated procedure.

The etiology of BMLs is currently poorly understood. However, it has been demonstrated that BMLs are made up of fibrous tissue and are osteonecrotic. They can be clearly identified in the hip, knee, and shoulder by use of magnetic resonance imaging (MRI). It stands to suffice that the first step in the aforementioned invention should be diagnosis and locating the BML to be treated.

It has been demonstrated that osteonecrotic tissue may be treated with autologous bone marrow. It also has been demonstrated that bone marrow can be used to treat fibrous bone tissue and cause it to remodel into healthy bone. It is hypothesized that the population of progenitor cells in the marrow help to regenerate bone tissue, reduce inflammation, and to remodel damaged bone to a healthy state.

The physical environment in which the bone marrow is placed is also crucial for proper healing of the bone marrow lesions. For progenitor cells to remodel into trabecular bone and its constituents, such as bone marrow and vasculature, it has been demonstrated that mechanical signals must be translated to the cell component.

The issue with current treatments is that the graft can often migrate and it is difficult to locate. Access methods themselves often contribute to creation of voids and gaps, which allow the cells within the therapeutic preparation to dissipate. It is desirable to retain the cellular components of the graft as long as possible at the application site in order to maximize effective contact between the therapeutic preparation and the pathology.

BMLs have been associated with and responsible for joint pain, lack of motion, lack of mobility, and other symptoms of osteoarthritis. Therefore, the treatment of BMLs in the bony tissue of joints can lead to a reduction of pain and pathology associated with osteoarthritis. Thus, treating BMLs with bone marrow has been shown to be effective in dealing with Arteriovenous Malformations (AVM). More importantly, therapeutic benefit is associated with the presence of specific types of cells in the bone marrow.

SUMMARY OF THE INVENTION

The proposed method incorporates cellular tissue that have been shown to promote bone healing, as well as a cell-retention method that will keep the cells in place to promote healing. It also is applicable for any joint in the body that is a meeting of 2 articulating bone surfaces. It also includes a device to perform the procedure that does not require multiple steps or tools to drill and to place the cellular tissue and retention device.

Furthermore it may be desirable to inject a limited amount of fluid into the space. Therefore, it may also be desirable to concentrate the cellular component which is injected into the site of pathology and ensure that the cellular component remains at the application site.

Throughout this application, the term "about" is used to indicate that a value includes the inherent variation of error for the device, the method being employed to determine the value, or the variation that exists among the study subjects. The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a device or a method that "comprises," "has," "contains," or "includes" one or more elements possesses those one or more elements, but is not limited to possessing only those one or more elements or steps. Likewise, an element of a device or method that "comprises," "has," "contains," or "includes" one or more features possesses those one or more features, but is not limited to possessing only those one or more features.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

DETAILED DESCRIPTION OF EXEMPLARY EMBODIMENTS

The method presented is applicable to a wide variety of BMLs, whether they are avascular or not. The inventive process and methods are an improvement on the art of using bone marrow and bone marrow concentrate, in that it provides a means of introducing a therapeutic preparation enriched for cellular components and enriched for growth factors and proteins present in plasma in combination with components that promote retention, such that a therapeutic preparation is substantially retained at the site of application. The sources of cellular components include autologous and allogeneic sources of cells. Improved healing of bone marrow lesions, called marrowplasty, will contribute to an improvement in the treatment of osteoarthritis.

In addition to the inventive placement of a therapeutic preparation composed of cellular material and a fluid retention material, the delivery of the therapeutic preparation is accomplished by the use of a drill device and assembly. The drill device includes a luer lock and Jacobs-Chuck combination on the proximal side of the drill.

Method

A first step of the procedure is the diagnosis. The diagnosis can be made by, for example, MRI. The practitioner should identify the location and severity of the BML. Additional methods of diagnosis include radiographs and other imaging methods.

Figure 1:
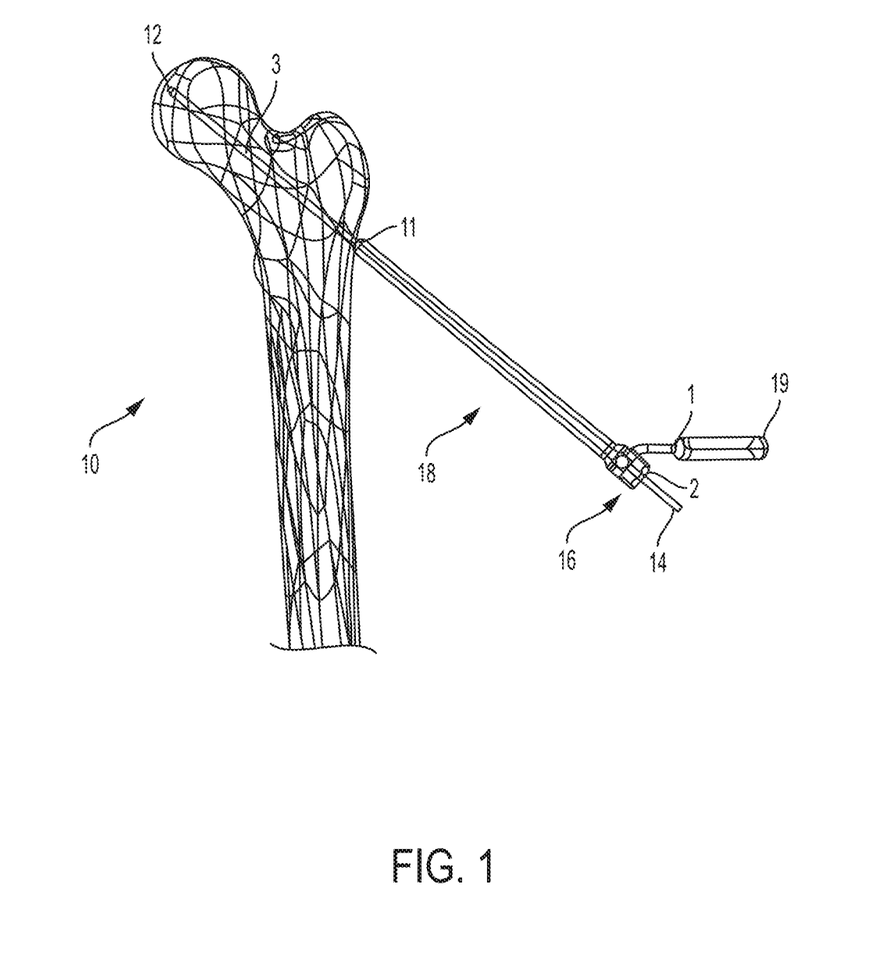
FIG. 1 illustrates a second step in a method for treating a BML in accordance with an embodiment of the claimed invention.
Figure 2:
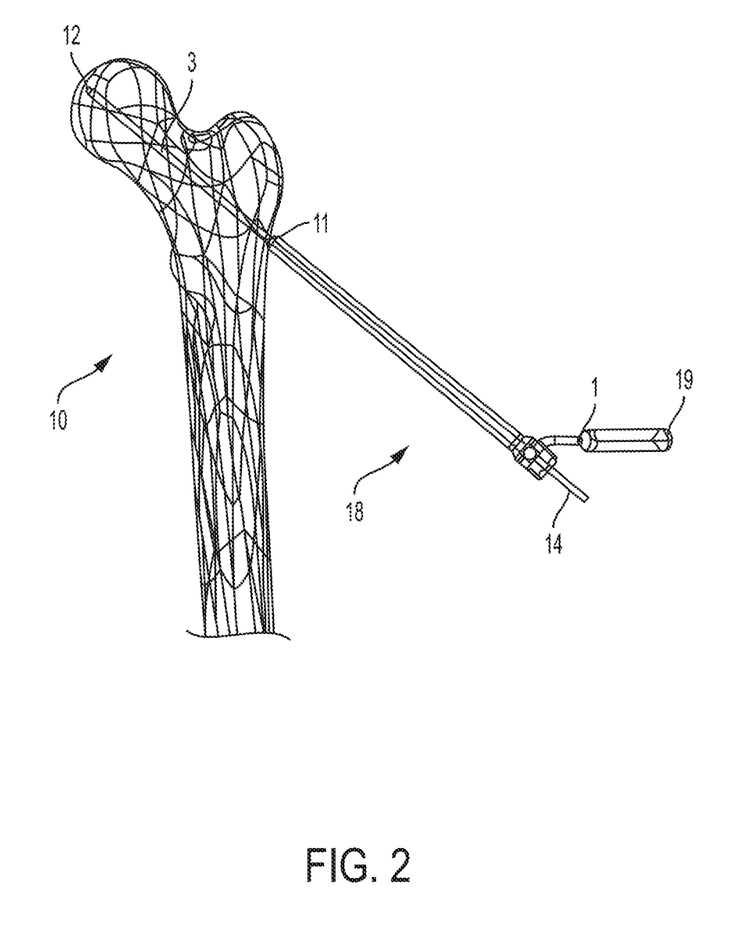
FIG. 2 illustrates a third step in a method for treating a BML in accordance with an embodiment of the claimed invention.
Figures 3A, 3B, 3C:
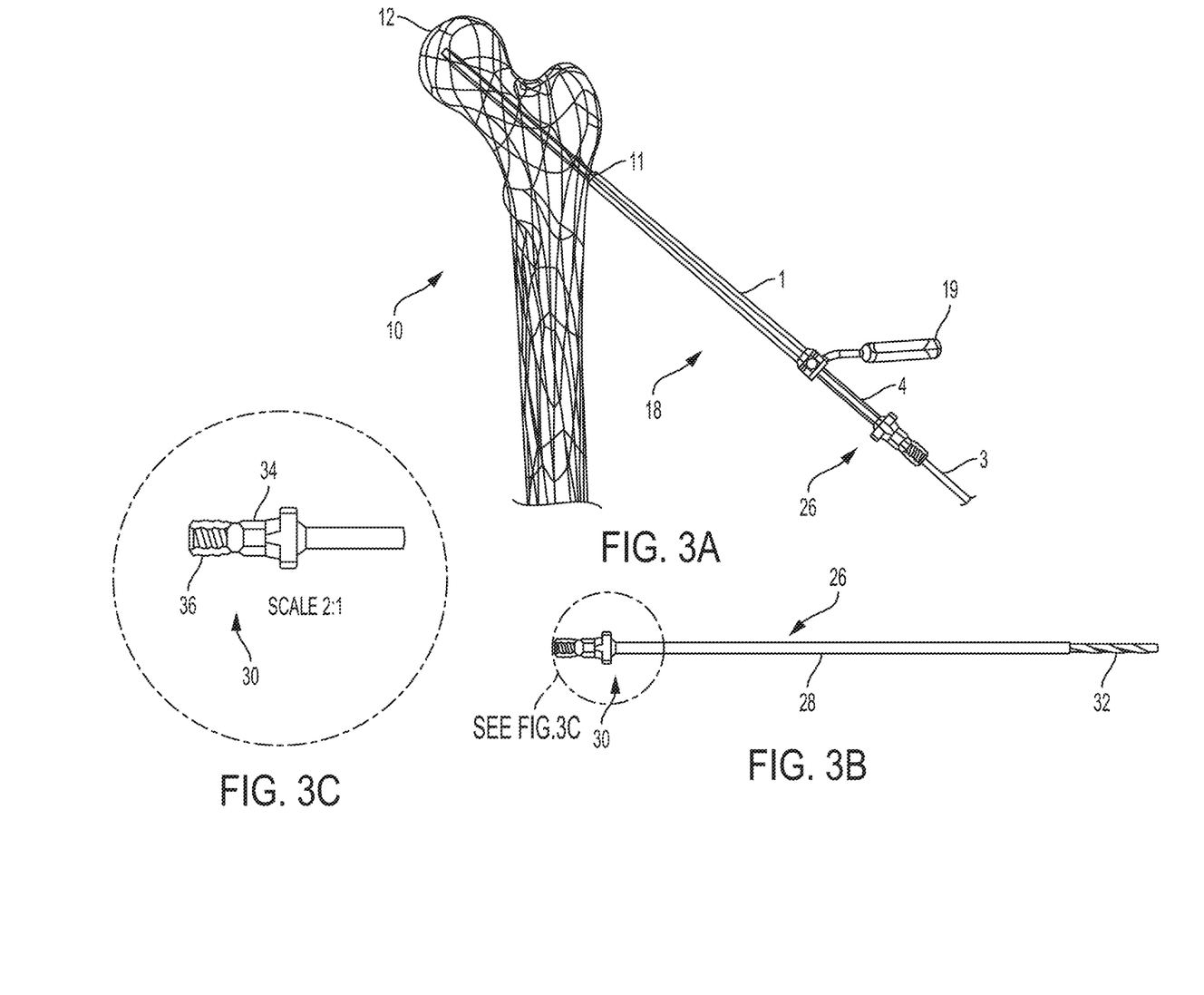
FIG. 3A illustrates a fourth step in a method for treating a BML in accordance with an embodiment of the claimed invention.
FIG. 3B illustrates a close-up view of a device that is used in the method illustrated in FIG. 3A in accordance with an embodiment of the claimed invention.
FIG. 3C illustrates a close-up view of the device illustrated in FIG. 3B in accordance with an embodiment of the claimed invention.

Referring now to FIG. 1, a second step in the treatment process is shown. A bone 10 with a lesion site 12 is shown. The second step includes placing a guide wire 14 near the lesion site 12. The guide wire 14 enters the bone 10 through an entry site 11. A wire guide 16 may be used to help place the guide wire 14. As shown, the wire guide 16 comprises a cannula that is inserted into a drill guide 18. The drill guide 18 comprises a cannula 20, a head 22, and an injection site 24. In some embodiments, the drill guide 18 further comprises a handle 19. The wire-guide cannula is sized to fit within the cannula 20 and further has a length sufficient to extend through the cannula 20 and into the bone 10 so that the guide wire 14 may be run into the bone 10 near the lesion site 12. In some embodiments, X-ray imaging is used to confirm that the guide wire 14 is appropriately placed relative to the lesion site 12. The drill guide 18 serves as a guide for a drill device 26 (e.g., see FIG. 3), which may be fitted with a changeable insert. After the guide wire 14 has been placed, a third step is to remove the wire guide 16 while leaving the drill guide 18 in place. FIG. 2 shows the drill guide 18 with the wire guide 16 removed.

Referring now to FIG. 3A, a fourth step in the treatment process is shown. In the fourth step, the drill device 26 is positioned within the drill guide 18. The drill device 26 includes a cannula 28, a head portion 30, and a bit 32. The cannula 28 is a hollow shaft with an outer diameter that complements an inner diameter to the cannula 20 of the guide 18. As shown in FIG. 3B, the cannula 28 includes a proximal end closest to a user and a distal end closest to the injury site. In some embodiments, the bit 32 is formed into a distal end of the cannula 28. In other embodiments, the bit 32 may be attached to the cannula 28 by screw attachment, welding, or otherwise. The bit 32 includes a hollow to permit substances to pass through the hollow. To insert the drill device 26, the bit 32 is aligned with the guide wire 14 inserted within the hollow portion of the bit 32. With the bit 32 so aligned, the drill device 26 may be guided by the guide wire 14 into the head 22 of the guide 18. The drill device 26 is then pushed into the cannula 28 until the bit 32 is proximate to an area to be drilled. The drill device 26 is then used to drill into the bone 10 until the bit 32 of the drill device 26 is coincident with the distal end of the guide wire 14. In some embodiments, the drill device 26 includes markings to confirm that the end of the drill is coincident with the end of the guide wire 14. For example, markings indicating millimeters may be distributed along a length of the cannula 28.

A close-up of the head portion 30 of the drill device 26 is shown in FIG. 3C. The head portion 30 includes both a fitting 34 for a standard Jacobs-Chuck and a luer fitting 36. The drill device 26 may be used with a powered or standard handle. In some embodiments, the use of the drill guide 18 and guide wire 14 are optional. While the drill guide 18 and the guide wire 14 can provide guidance to the drill device 26, they are not intrinsic to the treatment process.

Figure 4:
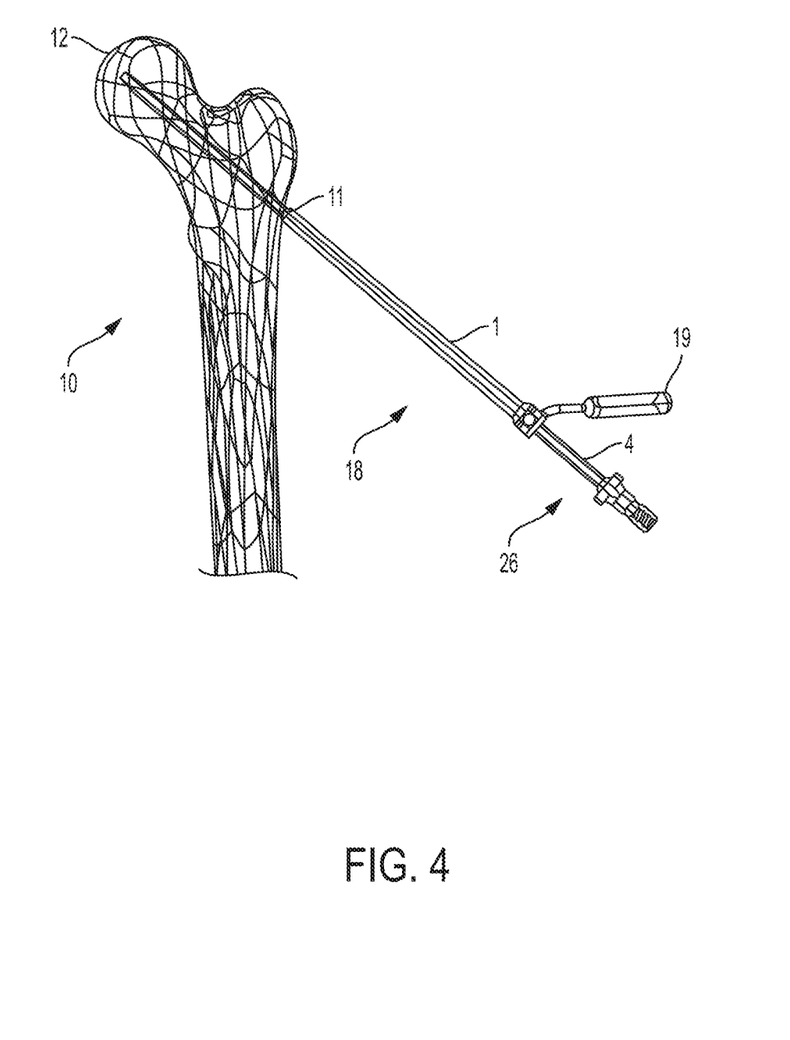
FIG. 4 illustrates a fifth step in a method for treating a BML in accordance with an embodiment of the claimed invention.

Referring now to FIG. 4, a fifth step in the treatment process is shown. In the fifth step, the guide wire 14 and the powered or standard handle (if fitted) are removed, leaving the drill device 26 and the drill guide 18 in place. In some embodiments, a position of the bit 32 relative to the lesion site 12 may be confirmed by radiograph.

Figure 5:
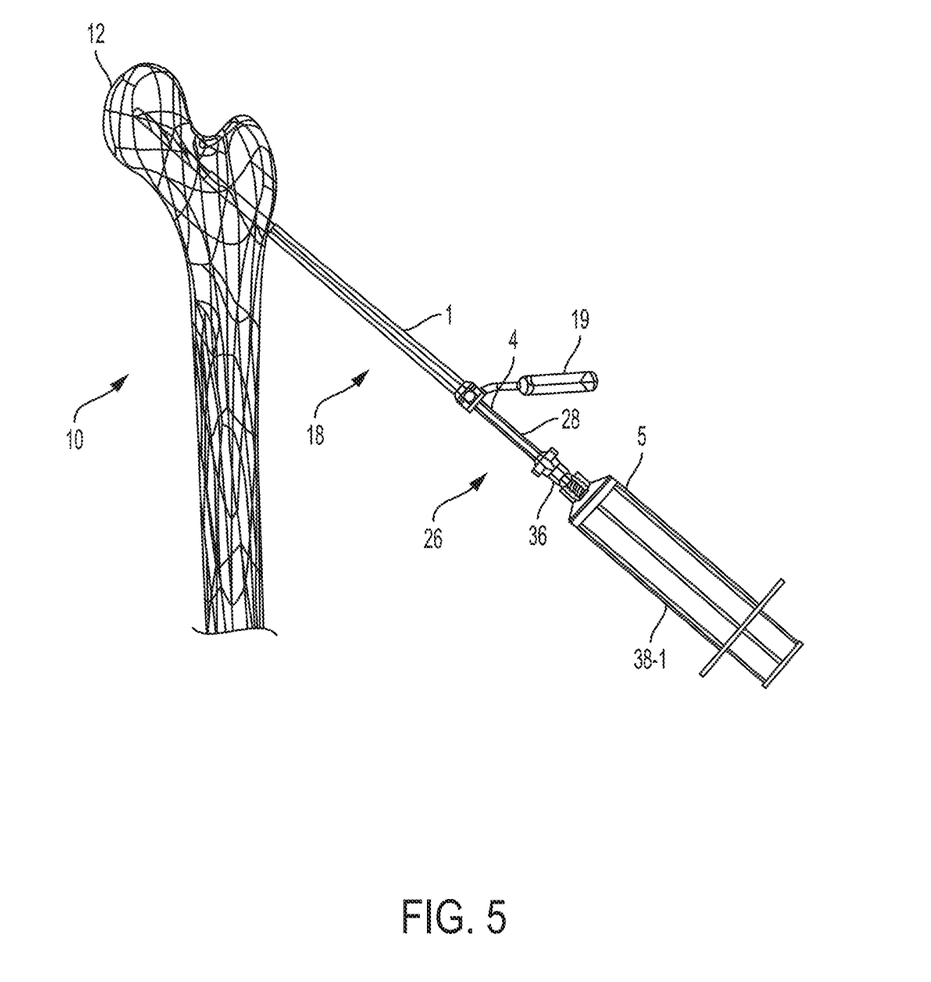
FIG. 5 illustrates a sixth step in a method for treating a BML in accordance with an embodiment of the claimed invention.

Referring now to FIG. 5, a sixth step in the treatment process is shown. In the sixth step, a cellular component is injected through the cannula 28 into an area in proximity with the lesion site 12. The injection can be done via a syringe 38-1 that attaches to the luer fitting 36.

Figure 6:
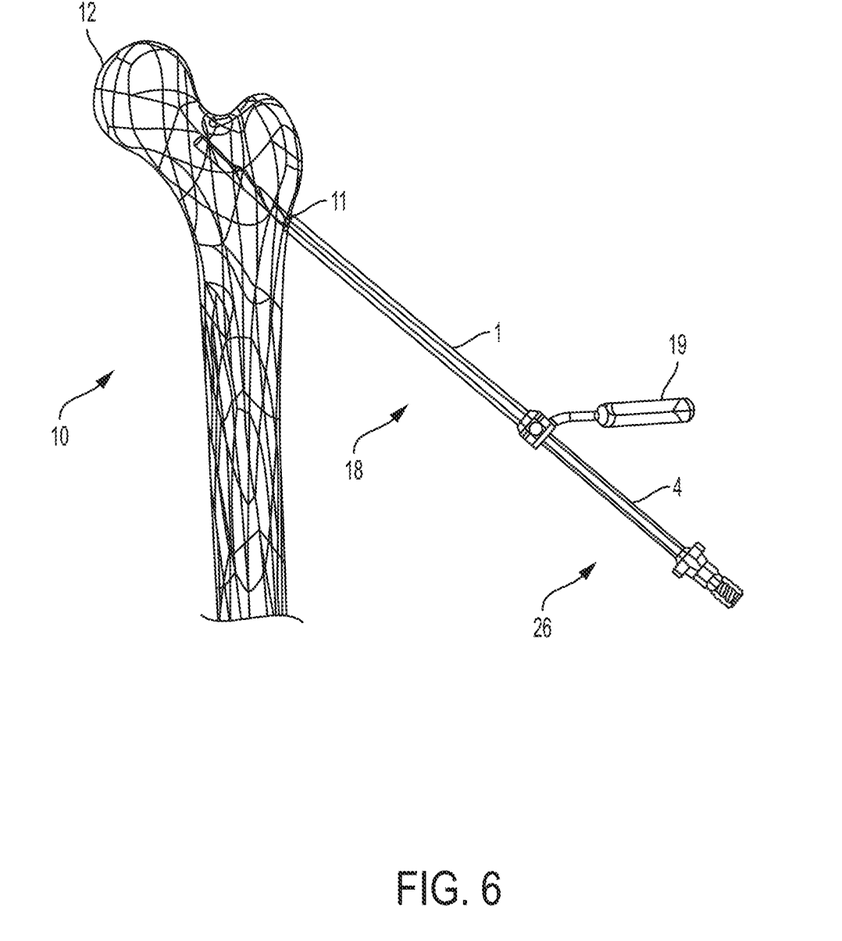
FIG. 6 illustrates a seventh step in a method for treating a BML in accordance with an embodiment of the claimed invention.

Referring now to FIG. 6, next, the operator retracts the bit 32 from the lesion site 12, but keeps the bit 32 within the bone 10. Preferably the bit 32 should be moved somewhere close to the entry site 11 so as to not allow the cellular component to seep around the tool. In some embodiments, the syringe 38-1 may be removed while the bit 32 is repositioned. In some embodiments the syringe 38-1 may remain attached to the drill device 26 while the bit 32 is repositioned.

Figure 7:
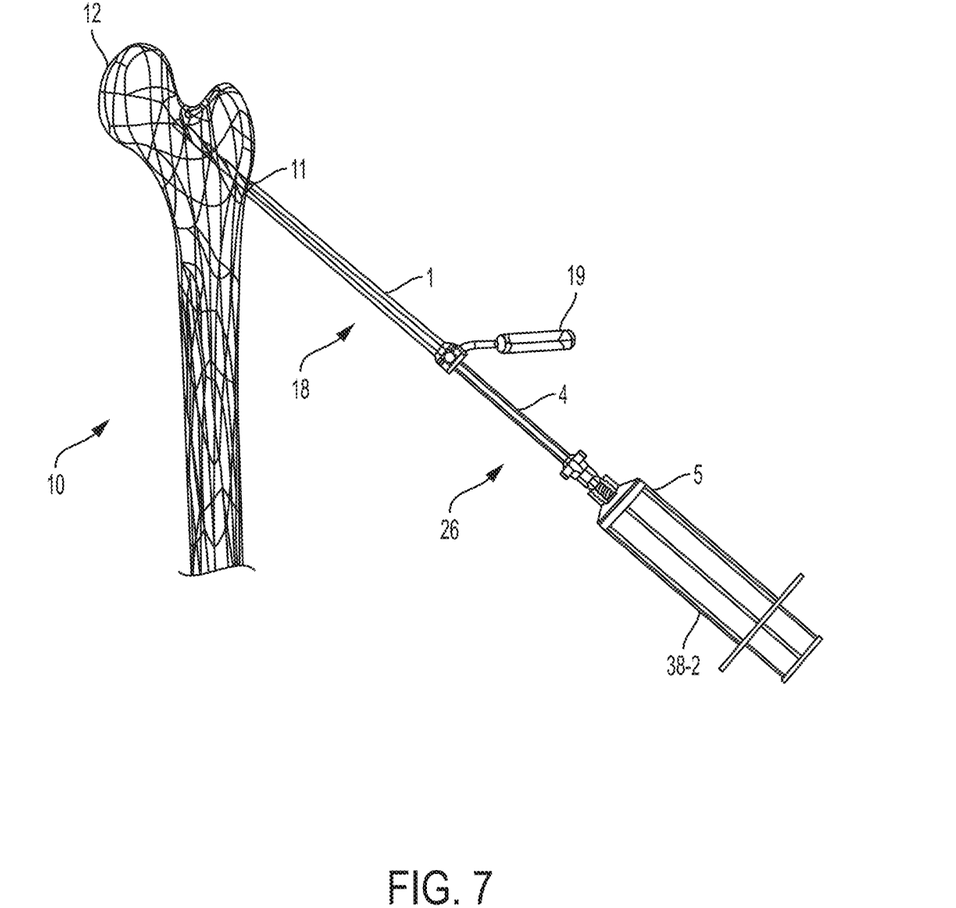
FIG. 7 illustrates an eighth step in a method for treating a BML in accordance with an embodiment of the claimed invention.

Referring now to FIG. 7, a seventh step in the treatment process is shown. In the seventh step, retention medium is injected with a syringe 38-2 to promote the retention of cells at the site of application. In some embodiments the retention medium is injected conjointly with the cellular component. In such embodiment, the syringe 38-1 may be include a mixture of the cellular component and the retention medium. After the injections have been completed, the drill device 26 and the drill guide 18 may be removed from the bone 10, leaving the cellular component and the retention medium in place. In some embodiments, a mechanical coupling is used to secure the retention medium and the cellular component to an environment near the injury site. In some embodiments, the mechanical coupling provides no structural support to the wound site. An exemplary form of mechanical coupling is adhesion. Adhesion between the retention medium and cellular component may be carried out using natural, biocompatible methods such as using integrins and cellular adhesion molecules.

In an embodiment of the drill device 26, a drill guide 18 with a secondary insert or wire guide 16 for a guide wire 14 is placed near a joint space and targeted towards a lesion site 12 of a bone 10. The guide wire 14 is placed with a distal tip of the wire in contact with the lesion. The wire guide 16 is then removed. The drill device 26 is then placed over the guide wire 14 and through the drill guide 16. The drill device 26 is then used to drill into the bone 10 until a distal end of the drill device 26 is coincident with the distal end of the guide wire 14. The guide wire 14 is then removed from the drill device 26. A syringe 38-1 is filled with a cellular component and is then attached to the end of the drill device 26, which has a receptor or head portion 30 which may receive either a power drill or a syringe. The cellular component is then injected into the area of the BML. The drill device 26 is then withdrawn to a periphery of the BML. A second syringe 38-2 is then attached which has a retention medium, which is then injected.

In another embodiment the above procedure is performed with no drill guide 18 or wire guide 16, but only with the guide wire 14 and the drill device 26.

In a third embodiment a secondary cannula (not shown) is inserted through the drill device 26. The secondary cannula may be flexible and made out of items such as shape memory plastic or nitionol. The intention of this tool is to more specifically target bone marrow lesions which may not be targeted by straight drilling.

In a fourth embodiment of the procedure the previous procedures are followed except that the cellular component and the cell retention medium are injected together.

In a fifth embodiment of the procedure, the drill device 26 is a biopsy needle with drill features. This may be used with the drill guide 18, but the drill guide 18 may not be necessary.

Cellular Component

In some embodiments, the cellular component described above is defined as a fluid containing cells which are known to be progenitors of bone-like tissue with a composition that is not naturally occurring in the body.

In some embodiments, the cellular component may include autologous bone marrow that has been concentrated and or filtered to remove red blood cells, but retains growth factors and mononuclear cells at a concentration greater than 1.1× that of plasma.

In some embodiments, the cellular component may include autologous bone marrow that has been concentrated and or filtered to remove the red blood cell and plasma components, leaving only known progenitor cells at a 1.1× or greater concentration.

In some embodiments, the cellular component may include autologous bone marrow that been extracted from the body and expanded to produce a concentration of progenitor cells at a concentration of greater than 1.1× that of natural tissues.

In some embodiments, the cellular component may include autologous adipose tissue that has been filtered, enzymatically digested, and or concentrated to isolate known progenitor cells at a concentration greater than 1.1× than natural adipose fluid and remove adipocytes, connective tissue, and other bodies known to not be progenitor cells.

In some embodiments, the cellular component may include any autologous tissue known to contain a population of progenitor cells which is concentrated to isolate the progenitor cells at a concentration of 1.1× or greater.

In some embodiments, the cellular component may include allogenic cell suspensions known to foster osteogenesis.

In some embodiments, the cellular component may include a combination of one or more of the above.

Retention Medium

In some embodiments, the retention medium forms a chemical bond to the cells in the area. In some embodiments, the retention medium forms a physical plug not allowing the cells to migrate from the area a component which coagulates or cross links the area in which the cells resides not allowing them to flow out, or which captures the cellular component or any combination of these characteristics.

In some embodiments, the retention medium is distinctly non-structural, allowing mechanical transmission from the outside environment to allow mechanical stimuli to cause progenitor cells to form bone as discussed in the back ground. For example, the retention medium can be include, but is not limited to, the following:

In some embodiments, the retention medium is physical plug. As there is a defect created by drilling into the lesion space it may be important to create a stoppage of the drill hole that is put into the bone. A physical plug stops leakage out of the defect side and hold the cell component within the lesion space. These items are preferably placed after the cell component has been placed and are typically placed on the proximal side of the bone marrow lesion between the lesion and the drill defect that was created earlier in the procedure. These materials may remain or biodegrade by natural processes.

In some embodiments, the retention medium may be an allograft bone plugs altered to fit the defect.

In some embodiments, the retention medium may be a threaded implantable screw, including an interference screw or an implantable plastic screw.

In some embodiments, the retention medium may use cell-surface binding. Cells are known to have binding receptors on their cell surface known as integrins. Specific materials are known to bind to these receptors. Binding of the specific materials to the integrins results in the cells being held or bound to the native environment by some chemical method after implantation. These retention factors may be injected prior to injection of the cellular component, with the cellular component, or after the cell component has been implanted.

In some embodiments, the retention medium may include tri-calcium phosphate materials that physically capture cells by binding to cell receptors of known progenitor cells. In some embodiments, a configuration would include an HA derived material.

In some embodiments, the retention medium may include synthetic beads that are functionalized to bind to cell receptors and or the native environment to hold the cells in place.

In some embodiments, the retention medium may be an alginate-based material. Alginate-base materials are known to bind to functional groups.

In some embodiments, the retention medium may be natural or synthetically derived hydrogels which are known to bind to integrins on the cell surface and or the native environment and which would remain local to the bone marrow lesion.

In some embodiments, the retention medium may include interwoven matrices. For example, the matrices may be physical matrices that are polymerized or set up and physically capture the cellular component. These materials may remain or naturally degrade as the material is replaced with healthy bone material.

In some embodiments, the retention medium may include gelatin. The gelatin may be xenographically derived, allographically derived, or autologously derived.

In some embodiments, the retention medium may include artificially created clots from auto graft material. Introducing calcium chloride and or thrombin or other thrombogenic factors to cause the concentrated components of the cellular material such as fibrin to polymerize and creates a matrix that does not allow movement of the cells.

In some embodiments, the retention medium may include allogenic fibrin glues which create a matrix that does not allow the cells to migrate from the injury site.

In some embodiments, the retention medium may include synthetic glues or hemostatic actors which are biocompatible.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

What is claimed is:

1. A method of treating a bone marrow lesion, the method comprising:
    drilling, using a drilling system, a subchondral channel into a bone, the drilling system comprising:
        a drill guide having a first cannula with a proximal end and a distal end;
        a wire guide having a second cannula with an outer diameter adapted to fit within the first cannula of the drill guide and further configured with a length that extends from an area proximate to an injury site to beyond the proximal end of the drill guide;
        a guide wire with diameter configured to fit within the second cannula and to extend from the injury site beyond a proximal end of the wire guide;
        a drill device having an outer diameter configured to fit within the first cannula and comprising:
            a third cannula extending through the drill device;
            a head portion at a proximal end of the drill device, the head portion comprising a Jacobs-Chuck and luer fitting; and
            a bit at a distal end of the drill device and comprising a hollow configured to allow the guide wire to pass therethrough;
    providing a cellular component to the injury site by injecting the cellular component through the third cannula of the drill device, the cellular component comprising autologous adipose tissue that has been filtered, enzymatically digested, and or concentrated to isolate progenitor cells at a concentration greater than 1.1× than natural adipose fluid and to remove adipocytes and connective tissue; and
    injecting a retention medium into the injury site via a syringe connected to the luer fitting to promote retention of the cellular component at the injury site.

2. The method of claim 1, further comprising, prior to the drilling, setting the guide wire into the bone with a distal end of the guide wire positioned close to the injury site and a proximal end of the guide wire positioned outside of the bone.

3. The method of claim 2, further comprising:
    subsequent to setting the guide wire, positioning the drill guide around the guide wire; and
    prior to drilling with the drill device, inserting the drill device into the drill guide.

4. The method of claim 3, wherein drilling into the bone further comprises placing the bit proximate to the distal end of the guide wire.

5. The method of claim 1, further comprising, prior to providing the cellular component, confirming placement of the bit proximate to the injury site via an imaging process.

6. The method of claim 1, wherein the retention medium further comprises an allogenic fibrin glue.

7. The method of claim 1, wherein the retention medium creates a chemical bond among cells of the injury site of the bone.

8. The method of claim 1, wherein the cellular component and the retention medium are injected to the injury site together.

9. The method of claim 1, wherein the retention medium comprises at least one of an integrin and a cellular adhesion molecule.

10. The method of claim 1, wherein the retention medium and the cellular component are mechanically coupled to an environment near the injury site.

11. The method of claim 1, wherein the third cannula of the drill device is made of a shape memory plastic.

12. The method of claim 1, wherein the third cannula of the drill device is made of nitinol.

* * * * *